United States Patent

Dhainaut et al.

Patent Number: 5,889,003
Date of Patent: Mar. 30, 1999

[54] FLAVONE COMPOUNDS

[75] Inventors: Alain Dhainaut, Chatou; Guy Lewin, Rueil-Malmaison; Emmanuel Canet, Paris; Michel Lonchampt, Chevilly-La-Rue; Yves Rolland, Vanves, all of France

[73] Assignee: Adir Et Compagnie, Courbevoie, France

[21] Appl. No.: 968,837

[22] Filed: Sep. 26, 1997

[30] Foreign Application Priority Data

Sep. 27, 1996 [FR] France .................................. 96 11808

[51] Int. Cl.$^6$ .......................... A61K 31/35; C07D 311/30
[52] U.S. Cl. .................. 514/233.5; 514/255; 514/259; 514/314; 514/320; 514/456; 544/151; 544/283; 544/376; 546/135; 546/196; 549/403
[58] Field of Search .................... 514/233.5, 255, 514/259, 314, 320, 456; 544/151, 283, 376; 546/135, 196; 549/403

[56] References Cited

U.S. PATENT DOCUMENTS 5,792,789  8/1998  Wierzbicki et al. .................... 514/456

OTHER PUBLICATIONS

Acta. Pharm. Hung., 1968, 32(2–3), 252–259.
Database Registry on STN® International, Chemical Abstracts Service, (Columbus, Ohio), Accession No. 70:68066 (File CA); Farkas, L. et al. Acta Pharm. Hung. 38(2–3), 252–259 (1968), abstract. 1969.

*Primary Examiner*—Michael G. Ambrose

[57] ABSTRACT

A compound of general formula (I):

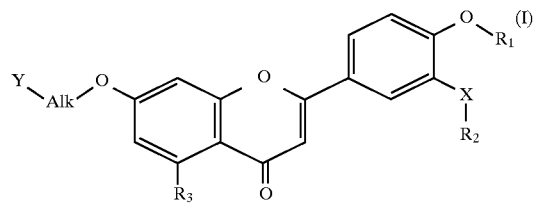

in which:
  $R_1$ represents alkyl,
  X represents oxygen, —CHR'— or —CR'=,
  R' is chosen from hydrogen and alkyl,
  $R_2$ represents optionally substituted alkyl as is defined in the description, cycloalkyl or polycycloalkyl as are defined in the description,
  $R_3$ represents hydrogen or hydroxyl,
  Alk represents alkylene, and
  Y is as defined in the description,
and medicinal products containing the same are useful as PDE IV inhibitors.

11 Claims, No Drawings

FLAVONE COMPOUNDS

BACKGROUND OF THE INVENTION

These new flavone compounds are group 4 phosphodiesterase (PDE4) inhibitors and, as a result, possess highly advantageous therapeutic applications.

In effect, the functions of most organic tissues are modulated by endogenous substances (hormones, neurotransmitters, autacoids) or exogenous substances. For some of these substances, the biological effect is relayed at intracellular level by enzyme effectors such as adenylate cyclase or guanylate cyclase. The stimulation of these enzymes, which are responsible for the synthesis of cyclic nucleotides such as cyclic adenosine 3',5'-monophosphate (cAMP) and cyclic guanosine 3',5'-monophosphate (cGMP), brings about a rise in the intracellular level of these second messengers involved in the regulation of a large number of biological functions (E. W. Sutherland and T. W. Rall, *Pharmacol. Rev.*, 12, (1960), 265).

The degradation of cyclic nucleotides is effected by a family of enzymes called phosphodiesterases (PDE), currently classified in 7 groups. The recognition of different isoforms within each of these groups, and of the tissue- or cell-specific distribution of certain isoforms, has stimulated the search for increasingly specific inhibitors of one or other type of isoenzyme (J. A. Beavo, *Physiological Rev.*, 75 (4), (1995), 725–749). Among the different PDE families, PDE4 has been identified in a very large number of tissues or cells, such as brain, heart, vascular endothelium, vascular and tracheobronchial smooth muscle and hematopoietic cells. Inhibition of the phosphodiesterases slows down the hydrolysis of the cyclic nucleotides and brings about an increase in the cAMP and/or cGMP content.

PDE4 inhibitors, which are responsible for an increase in cAMP levels, possess anti-inflammatory activities and relaxant effects on tracheobronchial smooth muscle, which accounts for their therapeutic value in the field of respiratory pathology or pathologies associated with an inflammatory process (M. N. Palfreyman, *Drugs of the Future*, 20 (8), (1995), 793–804; J. P. Barnes, *Eur. Respir. J.*, 8, (1995), 457–462; S. B. Christensen and T. J. Torphy, *Annual Reports in Medicinal Chemistry*, 29, (1994), 185–194, Academic Press).

DESCRIPTION OF THE PRIOR ART

Compounds possessing a flavone structure are very widely described in the literature. For example, Patent EP-B-319 412 describes flavonoids which are substituted in various ways, in particular with piperazinyl radicals and/or sugar residues such as those of β-glucose or rutinose. These compounds are useful in the treatment of vascular complaints (venous insufficiency, edema of the lower limbs, hemorrhoidal disease).

Moreover, the work of U. R. Kuppusamy et al. (*Biochem. Pharmacol.*, 44(7), (1992), 1307–1315) and of Yohko Sakamoto et al. (*Bull. Chem. Soc. Jpn.*, 62(8), (1989), 2450–2454) shows the activity of certain flavonoids on cAMP phosphodiesterase. The flavonoids tested are, for example, quercetin, luteolin, scutellarein, phloretin or genistein.

With the object of obtaining selective PDE4 inhibitors which are more potent and more active, the Applicant has discovered new flavone compounds of altogether novel structure and which are endowed with very advantageous pharmacological activities in the field of inhibition of group 4 phosphodiesterases.

DETAILED DESCRIPTION OF THE INVENTION

More especially, the present invention relates to the compounds of general formula (I):

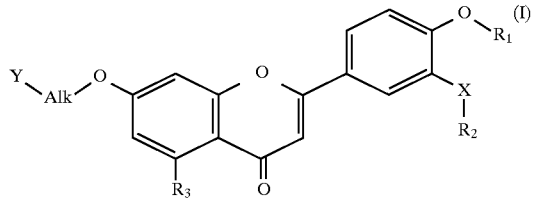

in which $R_1$ represents an alkyl radical, $R_2$ is chosen from
- a cyclic hydrocarbon radical containing from 3 to 9 carbon atoms, optionally containing one or more intracyclic double bonds and optionally substituted with one or more halogen atoms, alkyl, alkoxy and/or hydroxyl radicals,
- a polycyclic hydrocarbon radical containing from 6 to 15 carbon atoms, optionally containing one or more double bonds and optionally substituted with one or more halogen atoms, alkyl, alkoxy and/or hydroxyl radicals,
- a linear or branched hydrocarbon radical containing from 1 to 13 carbon atoms, optionally containing one or more unsaturations in the form of double and/or triple bonds and optionally substituted with one or more halogen atoms, hydroxyl, alkoxy, aryl, heteroaryl radicals, cyclic hydrocarbon radicals defined above and/or polycyclic hydrocarbon radicals defined above, $R_3$ is chosen from hydrogen and a hydroxyl radical, Alk represents a linear or branched alkylene radical containing from 1 to 6 carbon atoms, X is chosen from oxygen, a radical —CR'═ and a radical —CHR'—, R' is chosen from hydrogen and an alkyl radical, and Y is chosen from the radicals:

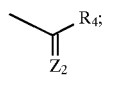

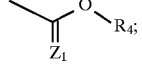

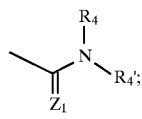

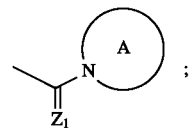

-continued

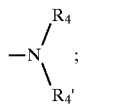

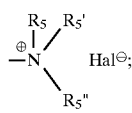

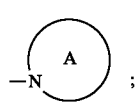

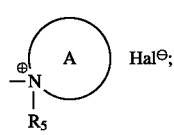

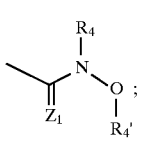

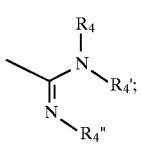

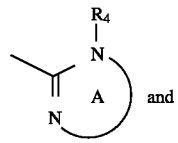

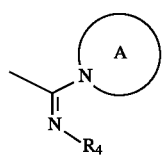

in which
- $Z_1$ represents oxygen or sulfur,
- $Z_2$ represents oxygen, sulfur, a radical =N—OR$_4$ or a radical

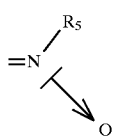

$R_4$, $R_4'$ and $R_4''$, which may be identical or different, are chosen, independently of one another, from hydrogen, an alkyl radical optionally substituted with an aryl or heteroaryl radical, an aryl radical, a heteroaryl radical and a cycloalkyl radical, $R_5$, $R_5'$, $R_5''$, which may be identical or different, are chosen, independently of one another, from an alkyl radical optionally substituted with an aryl radical or a heteroaryl radical, an aryl radical, a heteroaryl radical and a cycloalkyl radical, A represents a saturated or unsaturated mono- or bicyclic radical containing a total of 5 to 10 atoms (among which, in total 1, 2 or 3 of them can optionally represent a hetero atom chosen from oxygen, sulfur and/or nitrogen) and optionally substituted with one or more halogen atoms, alkyl and/or alkoxy radicals, and Hal represents a halogen atom,
or alternatively the radicals -Alk-Y together form a radical chosen from:

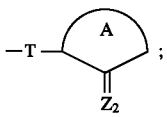

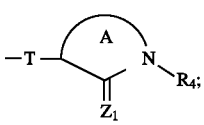

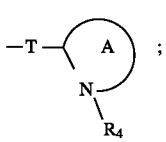

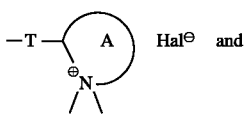

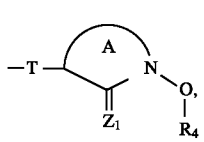

in which A, $R_4$, $R_5$, $R_5'$, $Z_1$, $Z_2$ and Hal are as defined above, and T represents either a bond or a linear or branched alkylene radical containing from 1 to 6 carbon atoms, on the understanding that, except where otherwise stated,
- the term "alkyl" represents an alkyl radical containing from 1 to 6 carbon atoms in an unbranched or branched chain, and optionally substituted with one or more halogen atoms, hydroxyl and/or alkoxy radicals,
- the term "alkoxy" represents an alkoxy radical containing from 1 to 6 carbon atoms in an unbranched or branched chain, and optionally substituted with one or more halogen atoms and/or hydroxyl radicals,
- the term "aryl" represents a phenyl or naphthyl radical, optionally substituted with one or more halogen atoms, alkyl, hydroxyl and/or alkoxy radicals,
- the term "heteroaryl" represents a radical chosen from furyl, thienyl, thiazolyl, isothiazolyl, oxazolyl, isoxazolyl, pyrrolyl, imidazolyl, pyrazolyl, pyridyl, pyrazinyl, pyrimidyl, pyridazinyl, indolyl, quinolyl, isoquinolyl and quinazolinyl, optionally substituted with one or more halogen atoms, alkyl, hydroxyl and/or alkoxy radicals,
- the term "halogen atom" represents a fluorine, chlorine, bromine or iodine atom,
- the term "cycloalkyl" represents a cyclic and saturated hydrocarbon radical containing from 3 to 8 carbon atoms and optionally substituted with one or more halogen atoms, alkyl, hydroxyl and/or alkoxy radicals, their possible optical and/or geometric isomers in pure form or as a mixture, and their possible addition salts with a pharmaceutically acceptable acid or base.

Among the acids which can be used to form a pharmaceutically acceptable addition salt with the compounds of the invention, there may be mentioned, by way of examples and without implied limitation, hydrochloric, sulfuric, phosphoric, tartaric, malic, maleic, fumaric, oxalic, methanesulfonic, ethanesulfonic, camphoric and citric acids.

Among the bases which can be used to form a pharmaceutically acceptable addition salt with the compounds of the invention, there may be mentioned, by way of examples and without implied limitation, sodium, potassium, calcium or aluminum hydroxides, alkali metal or alkaline-earth metal carbonates and organic bases such as triethylamine, benzylamine, diethanolamine, tert-butylamine, dicyclohexylamine and arginine.

The subject of the present invention is also the process for preparing the compounds of formula (I), wherein the compound of formula (II):

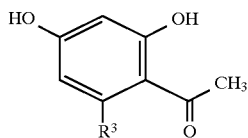
(II)

in which $R_3$ is as defined above,
is reacted, according to the procedure described by M. Cushman et al. (*Tetrahedron Lett.*, 31(45), (1990), 6497–6500), with the compound of formula (III):

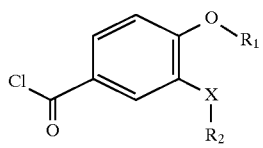
(III)

in which $R_1$, $R_2$ and X are as defined above,
in the presence of an excess of lithium bis(trimethylsilyl) amide so as to obtain the compound of formula (IV):

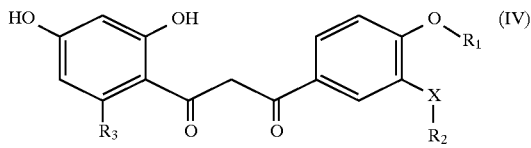
(IV)

in which $R_1$, $R_2$, $R_3$ and X are as defined above,
which is cyclized, by heating in glacial acetic acid and in the presence of sulfuric acid, to the compound of formula (V):

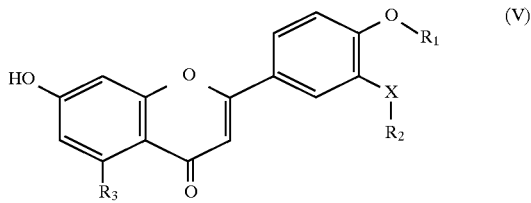
(V)

in which $R_1$, $R_2$, $R_3$ and X are as defined above,
which is finally coupled:
either with a compound of formula (VIa):

Y—Alk—Hal (VIa)

in which Y and Alk are as defined above and Hal represents a halogen atom chosen from chlorine, bromine and iodine, in the presence of potassium hydrogen carbonate in the heated state, under an inert atmosphere and in an aprotic polar solvent such as dimethylformamide, or with a compound of formula (VIb):

Y—Alk—OH (VIb)

in which Y and Alk are as defined above, in the presence of ethyl azodicarboxylate and triphenylphosphine ("Mitsunobu" reaction), so as to yield the compounds of formula (I), which can be, where appropriate and if so desired:

separated according to one or more purification methods chosen from crystallization, chromatography on silica gel, extraction, filtration and passage through charcoal or resin, separated, in pure form or in the form of a mixture, into their possible optical and/or geometric isomers, according to standard separation techniques, and/or converted with an acid or a base to pharmaceutically acceptable salts.

The compounds of formula (V) for which X represents oxygen, $R_1$ represents a methyl radical and $R_3$ represents a hydroxyl radical may advantageously be obtained from diosmetin, which is reacted with benzyl bromide in the presence of potassium hydrogen carbonate in dimethylformamide to obtain the compound of formula (VII):

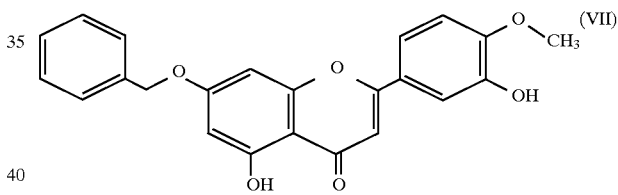
(VII)

which is then treated with a halide of formula (VIII):

$R_2$—Hal (VIII)

in which $R_2$ is as defined above and Hal represents a halogen atom chosen from chlorine, bromine and iodine, in the presence of potassium hydrogen carbonate in dimethylformamide, yielding the compound of formula (IX):

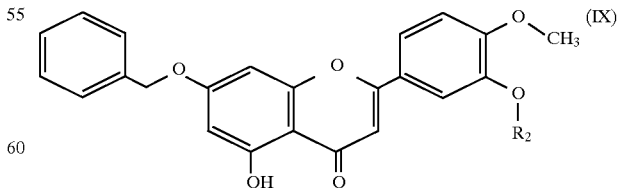
(IX)

in which $R_2$ is as defined above, to yield, after debenzylation under the action of hydrogen and in the presence of palladium on charcoal, the compound of formula (X):

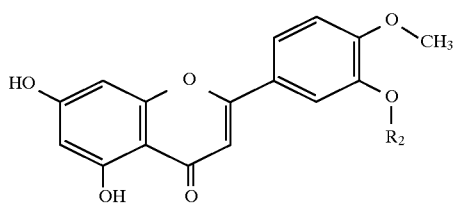  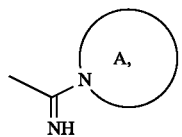

in which $R_2$ is as defined above,
a particular case of the compounds of formula (V) for which X represents oxygen, $R_1$ represents a methyl radical and $R_3$ represents a hydroxyl radical.

The compounds of formula (I) for which Y represents the radicals:

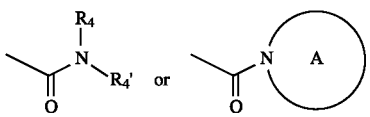

in which A, $R_4$ and $R_4'$ are as defined above,
may also be obtained from the corresponding compounds of formula (I) for which Y represents the radical

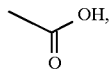

by performing a peptide coupling (for example according to the method described by M. Bodanszky and A. Bodanszky, *The Practice of Peptide Synthesis*, Springer-Verlag, 1984), and more especially a peptide coupling using dicyclohexylcarbodiimide (DCC) or one of its derivatives. The amide link may also be produced in the presence of 2-(1H-benzotriazol-1-yl)-1,1,3,3-tetramethyluronium tetrafluoroborate (TBTU), optionally in the presence of an activator such as hydroxybenzotriazole (HOBT) according to the methods described by M. S. Bernatowicz et al. (*Tetrahedron Lett.*, 30, (1989), 4645), A. G. Beck-Sickinger et al. (*Pept. Res.*, 4, (1991), 88), G. E. Reid et al. (*Anal. Biochem.*, 200, (1992), 301) or alternatively by C. G. Fields et al. (*Pept. Res.*, 4, (1991), 95). It can also be especially advantageous to form the amide link in the presence of propylphosphonic anhydride and N-ethylmorpholine according to the method described by H. Wissmann et al. (*Angew. Chem. Int. Ed.*, 19, (1980), 133–134).

The compounds of formula (I) for which Y represents a radical —C(O)NR$_4$OR$_4'$, in which R$_4$ and R$_4'$ are as defined above, may also be obtained from the corresponding compounds of formula (I) for which Y represents a radical —C(O)OR$_4$, in which R$_4$ is as defined above, by reacting them with a compound of formula NHR$_4$—OR$_4'$, R$_4$ and R$_4'$ being as defined above.

The compounds of formula (I) for which Y represents a radical

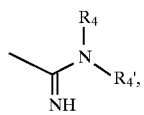

$R_4$ and $R_4'$ being as defined above, or a radical

in which A is as defined above, may also be obtained from the corresponding compounds of formula (I) for which Y represents a —C≡N radical, by treatment with an amine of formula HNR$_4$R$_4'$, R$_4$ and R$_4'$ being as defined above, or, respectively, with a cyclic amine of formula

HN—A,

A being as defined above.

Generally speaking, the compounds of formula (I) for which $Z_1$ or $Z_2$ represents sulfur may advantageously be obtained from the corresponding compounds of formula (I) for which $Z_1$ or $Z_2$ represents oxygen, by treatment with Lawesson's reagent.

The compounds of formula (I) for which $Z_2$ represents a radical =N—OR$_4$ or a radical

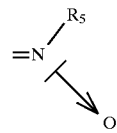

in which $R_4$ and $R_5$ are as defined above, are advantageously obtained from the corresponding compounds of formula (I) for which $Z_2$ represents oxygen, by the action of $H_2N$—OR$_4$ or, respectively, of $R_5$—NHOH, $R_4$ and $R_5$ being as defined above.

The compounds of formula (I) in which Y contains a quaternary ammonium function are advantageously obtained from the corresponding compounds of formula (I) in which Y contains a tertiary amine function, which is treated with a halide of formula Hal-R$_5$, in which Hal represents a chlorine, bromine or iodine atom and R$_5$ is as defined above.

The compounds of the present invention are very potent group 4 phosphodiesterase inhibitors and, as a result, are especially advantageous in therapeutic applications relating to inflammation and bronchial relaxation, and more specifically in asthma and chronic obstructive bronchopathies (A. J. Duplantier et al., *Annu. Rep. Med. Chem.*, 29, (1994), 73–81), (C. D. Nicholson et al., *Pulmonary Pharmacol*, 7, (1994), 1–17), (T. J. Torphy et al., *Drug News Perspect.*, 6, (1993), 203–214), (J. A. Lowe et al., *Drugs Future*, 17, (1992), 799–807), but also in all complaints such as rhinitis (I. Raderer et al., *Wien. Med. Wochenschr.*, 145, (1995), 456–458), acute respiratory distress syndrome (ARDS) (C. R. Turner et al., *Circulatory Shock*, 39, (1993), 237–245), allergies and dermatitis (J. M. Hanifin et al., *J. Invest. Dermatol.*, 105, (1995), 84S-88S), (J. M. Hanifin, *J. Dermatol. Sci.*, 1, (1990), 1–6), psoriasis (E. Touitou et al., *J. Pharm. Sci.*, 81, (1992), 131–134), (F. Levi-schaffer et al., *Skin Pharmacol.*, 4, (1991), 286–290), rhumatoid arthritis (J. M. Anaya et al., *J. Rheumatol.*, 22, (1995), 595–599), autoimmune diseases, (C. P. Genain et al. *Proc. Natl. Acad. Sci.*, 92, (1995), 3601–3605), multiple sclerosis (N. Sommer et al., *Nat. Med.*, 1, (1995), 244–248), dyskinesias (T. Kitatani et al., *Nippon Yakurigaku Zasshi*, 86, (1985), 353–358), glomerulonephritis (M. Hechtet et al., *J. Leukoc. Biol.*, 57, (1995), 242–249), osteoarthritis and septic shock (A. M. Badger et al., *Circ. Shock*, 44, (1994), 188–195), (L. Sekut et al., *Clin. Exp. Immunol.*, 100, (1995), 126–132), AIDS (T. F. Greten et al., *Aids*, 9, (1995), 1137–1144), depression (N. A. Saccomano et al., *J. Med. Chem.*, 34, (1991), 291–298), and any neurodegenerative disease accompanied by inflammatory phenomena, such as Alzheimer's, Parkinson's, Huntington's and Down's diseases and amyotrophic lateral sclerosis (G. Z. Feuerstein et al., *Ann. N.Y. Acad. Sci.*, 765, (1995), 62–71).

These therapeutic indications are not limiting, inasmuch as a decrease in cellular cAMP concentration, irrespective of its cause and its tissue localization, can result in a cellular dysfunction, a source of pathological phenomena, and can constitute a major therapeutic target for the products of the invention.

The subject of the present invention is also pharmaceutical compositions containing the products of formula (I) or, where appropriate, one of their addition salts with a pharmaceutically acceptable acid or base, in combination with one or more pharmaceutically acceptable excipients.

Among the pharmaceutical compositions according to the invention, there may be mentioned, more especially, those which are suitable for oral, parenteral, nasal, per- or transcutaneous, rectal, perlingual, ocular or respiratory administration, and in particular simple or sugar-coated tablets, sublingual tablets, sachets, packets, hard gelatin capsules, preparations to be dissolved under the tongue, lozenges, suppositories, creams, ointments, skin gels, ampoules of liquid to be swallowed or for injection and aerosols.

The dosage varies according to the patient's sex, age and weight, the administration route, the nature of the therapeutic indication or any treatments which may possibly be used in combination, and ranges between 1 mg and 5 g per 24 hours in 1 or 2 doses.

The examples which follow illustrate the invention without, however, limiting it in any way. The starting materials used in these examples are either commercial or directly accessible using procedures known to a person skilled in the art.

Preparation A: 3'-O-Cyclopentyidiosmetin
Step a: 7-O-Benzyldiosmetin

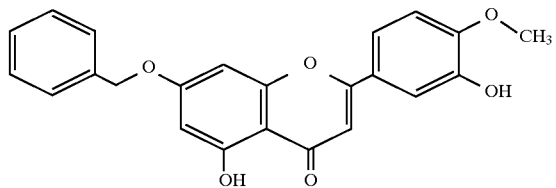

7 g (70 mmol) of potassium hydrogen carbonate are added to 21 g (70 mmol) of diosmetin in 200 ml of dimethylformamide. The reaction mixture is stirred at 110°–120° C. under nitrogen for 5 minutes. Next, 12.5 ml (105 mmol) of benzyl bromide are added and the reaction is continued under the same conditions for 2.5 hours. The reaction mixture is then filtered through sintered glass and evaporated to dryness. The residue is taken up with 300 ml of tetrahydrofuran and then 50 ml of ethanol, and the mixture is heated to reflux for approximately 15 minutes and then filtered while hot. The tetrahydrofuran is eliminated from the filtrate by successive additions of 250 ml of ethanol and concentration to the point where crystallization has clearly begun. After one night at room temperature, the crystals are filtered off. 12 g of the expected product are obtained.

Yield: 44% Melting point: 208°–212° C.

Step b: 7-O-Benzyl-3'-O-cyclopentyidiosmetin

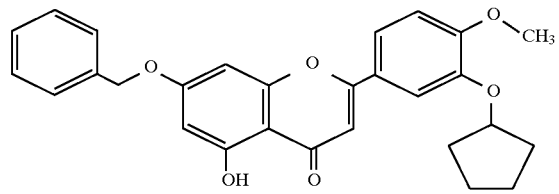

12 g (120 mmol) of potassium hydrogen carbonate are added to 11.7 g (30 mmol) of 7-O-benzyldiosmetin obtained in the preceding step in 150 ml of dimethylformamide. The reaction mixture is stirred at 110°–120° C. under nitrogen for 5 minutes. 4.3 ml (39 mmol) of cyclopentyl bromide are then added and the reaction is continued under the same conditions for 2 hours. Two further additions of 1.8 g of potassium hydrogen carbonate and of 0.64 ml of cyclopentyl bromide are thereafter made one hour apart. After a further hour of reaction, the reaction mixture is taken up with 1.5 l of water and extracted with dichloromethane. The organic phase is concentrated and the dry reaction residue is solubilized in dichloromethane, which is removed by successive additions of methanol until crystallization takes place. A recrystallization is performed under the same conditions to give 9.73 g of the expected compound.

Yield: 71% Melting point: 208°–209° C.

Step c: 3'-O-Cyclopentyldiosmetin

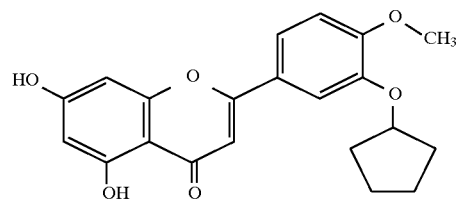

8.25 g (18 mmol) of the compound obtained in the preceding step are solubilized in the heated state in 300 ml of dimethylformamide. To this solution while still warm, 900 mg of 10% palladium on charcoal are added. The mixture is subjected to hydrogenation at room temperature and atmospheric pressure for 2.5 hours, filtered and evaporated to dryness. The dry residue is then solubilized in a dichloromethane/methanol mixture, thereafter diluted with methanol and lastly concentrated to remove the dichloromethane. 4.96 g of the expected crystallized compound are obtained.

Yield: 75% Melting point: 200°–201° C.

Preparation B: 3'-O-Cyclopentyl-5-deoxydiosmetin

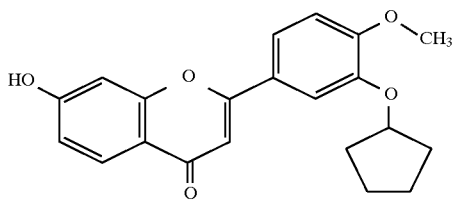

A solution of lithium bis(trimethylsilyl)amide in tetrahydrofuran (1M, 80 ml, 80 mmol) is added over 15 minutes to a solution of 3.04 g (20 mmol) of 2,4-dihydroxyacetophenone in tetrahydrofuran under argon at −78° C. The reaction mixture is stirred for one hour at −78° C. and two hours at −10° C., cooled again to −78° C. and then treated with a solution of 5.09 g (20 mmol) of 3-cyclopentyloxy-4-methoxybenzoyl chloride in 15 ml of tetrahydrofuran. Stirring is maintained for half an hour at −78° C., then 4 hours while allowing the reaction mixture to return to room temperature.

After hydrolysis, extraction and drying of the diketo intermediate, the latter is treated with 100 ml of glacial acetic acid and 0.5 ml of sulfuric acid at a temperature of 100° C. for 1 hour. The reaction mixture is concentrated to one quarter of its initial volume and diluted in 500 ml of ice-cold water. The precipitate is filtered off and washed with water, then dried.

Yield: 68% Melting point: 228°–229° C.

Preparation C: 3'-O-(5-Phenyl-2-pentyl)diosmetin

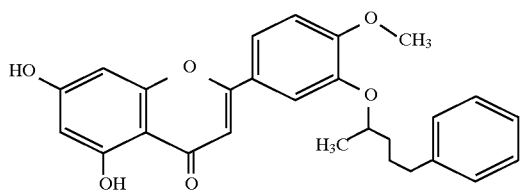

Using the procedure described in Preparation A, replacing cyclopentyl bromide by 2-chloro-5-phenylpentane, the expected compound is obtained.

EXAMPLE 1

7-O-(2-Oxopropyl)-3'-O-cyclopentyidiosmetin

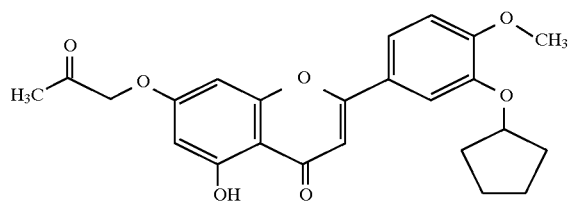

0.92 g of chloro-2-propanone is added to a mixture containing 3.7 g of 3'-O-cyclopentyldiosmetin obtained in Preparation A and 1.3 g of potassium hydrogen carbonate. The mixture is stirred under an inert atmosphere at 120° C. for 3 hours, then cooled to room temperature and diluted with 50 ml of dichloromethane. The insoluble matter is filtered off and the filtrate is concentrated to dryness. The residue obtained is taken up in methanol. The expected product crystallizes, and is then filtered off and dried under vacuum.

Melting point: 170°–171° C.

EXAMPLE 2

7-O-Ethoxycarbonylmethyl-3'-O-cyclopentyidiosmetin 2.2 g of ethyl azodicarboxylate are added to a mixture containing 3.7 g of 3'-O-cyclopentyidiosmetin obtained in Preparation A, 2.6 g of triphenylphosphine and 1.1 g of ethyl glycolate in 50 ml of tetrahydrofuran. This mixture is stirred for 24 hours at room temperature under an inert atmosphere. The reaction mixture is then concentrated and purified by flash chromatography (eluent: dichloromethane/methanol, 99:1). The expected compound is recrystallized in methanol.

Melting point: 146°–147° C.

Working according to the procedure described in Example 1, replacing 1-chloro-2-propanone by the appropriate halogenated compound, the compounds which follow are obtained.

EXAMPLE 3

7-O-Cyanomethyl-3'-O-cyclopentyidiosmetin

Melting point: 189°–190° C.

EXAMPLE 4

7-O-t-Butoxycarbonylmethyl-3'-O-cyclopentyldiosmetin

Melting point: 160°–161° C.

EXAMPLE 5

7-O-(3-Ethoxycarbonylpropyl)-3'-O-cyclopentyldiosmetin

Melting point: 78°–79° C.

EXAMPLE 6

7-O-Benzoylmethyl-3'-O-cyclopentyldiosmetin

Melting point: 185°–186° C.

EXAMPLE 7

7-O-(4-Oxopentyl)-3'-O-cyclopentyldiosmetin

Melting point: 109°–110° C.

EXAMPLE 8

7-O-(3-Oxo-2-butyl)-3'-O-cyclopentyldiosmetin

Melting point: 120°–121° C.

EXAMPLE 9

7-O-(2-Oxocyclopentyl)3'-O-cyclopentyldiosmetin

Melting point: 190°–191° C.

EXAMPLE 10

7-O-(2-Oxobutyl)-3'-O-cyclopentyldiosmetin

Melting point: 192°–193° C.

EXAMPLE 11

7-O-(Carboxymethyl)-3'-O-cyclopentyldiosmetin

Elemental analysis: (empirical formual: $C_{23}H_{22}O_8$ molecular weight: 426)

|  | C | H |
|---|---|---|
| % found | 64.71 | 5.46 |
| % calculated | 64.78 | 5.20 |

EXAMPLE 12

7-O-(N-Methoxy-N-methylaminocarbonylmethyl)-3'-O-cyclopentyldiosmetin

Melting point: 194°–195° C.

EXAMPLE 13

7-O-Morpholinocarbonylmethyl-3'-O-cyclopentyldiosmetin

By performing a peptide coupling between the acid obtained in Example 11 and morpholine, the expected compound is obtained.

Melting point: 128°–130° C.

EXAMPLE 14

7-O-(N,N-Diethylaminocarbonylmethyl)3'-O-cyclopentyldiosmetin

Working as described in the preceding example, replacing morpholine by diethylamine, the expected compound is obtained.

Melting point: 79°–80° C.

EXAMPLE 15

7-O-(N,N-Diethylaminothiocarbonylmethyl)3'-O-cyclopentyldiosmetin

The amide obtained in Example 14 is treated with Lawesson's reagent in order to yield the expected compound.

Melting point: 85°–87° C.

EXAMPLE 16

7-O-[(4-Methyl-1-piperazinyl)carbonylmethyl]-3'-O-cyclopentyldiosmetin

Replacing morpholine in Example 13 by N-methylpiperazine, the expected compound is obtained.

Melting point: 144°–145° C.

In the same way, using the appropriate amines, the compounds of Examples 17 to 19 which follow are obtained.

EXAMPLE 17

7-O-(N-Methylaminocarbonylmethyl)-3'-O-cyclopentyldiosmetin

Melting point: 209°–210° C.

EXAMPLE 18

7-O-Aminocarbonylmethyl-3'-O-cyclopentyldiosmetin

Melting point 215°–217° C.

EXAMPLE 19

7-O-(N,N-Dimethylaminocarbonylmethyl)3'-O-cyclopentyldiosmetin

Melting point: 187°–188° C.

EXAMPLE 20

7-O-(N-Hydroxyaminocarbonylmethyl)-3'-O-cyclopentyldiosmetin

The ester obtained in Example 2 is treated with hydroxylamine to yield the expected hydroxamic acid.

Melting point: 189°–191° C.

Carrying out the procedure described in Example 2, replacing ethyl glycolate by the appropriate amino alcohol, the compounds which follow are obtained.

EXAMPLE 21

7-O-(Morpholinoethyl)-3'-O-cyclopentyldiosmetin

Melting point: 145°–146° C.

EXAMPLE 22

7-O-[(4-Methyl-1-piperazinyl)ethyl]3'-O-cyclopentyldiosmetin

EXAMPLE 23

7-O-(N,N-Dimethylaminoethyl)-3'-O-cyclopentyldiosmetin

Melting point: 154°–155° C.

EXAMPLE 24

7-O-(N,N,N-Trimethylammonioethyl)-3'-O-cyclopentyldiosmetin iodide

Compound obtained by treating the compound of Example 23 with methyl iodide. Melting point:>166° C. (decomposition)

EXAMPLE 25

7-O-(N-Methyl-2-piperidylmethyl)-3'-O-cyclopentyldiosmetin

Compound obtained by carrying out the procedure described in Example 2, replacing ethyl glycolate by 2-hydroxy-N-methylpiperidine.

EXAMPLE 26

7-O-(N-Ethoxyaminocarbonylmethyl)-3'-O-cyclopentyldiosmetin

The compound obtained in Example 3, treated with O-ethylhydroxylamine, yields, after hydrolysis, the expected compound.

EXAMPLE 27

7-O-(N-Methylcarbamimidoylmethyl)-3'-O-cyclopentyldiosmetin

The compound obtained in Example 3, treated with methylamine, yields the expected amidine.

Working as described in Example 27, replacing methylamine by the appropriate amine, the compounds which follow are obtained.

EXAMPLE 28

7-O-(N$^1$,N$^1$-Diethylcarbamimidomethyl)-3'-O-cyclopentyldiosmetin

EXAMPLE 29

7-O-(2-Morpholino-2-iminoethyl)-3'-O-cyclopentyldiosmetin

EXAMPLE 30

7-O-(2-Hydroxyiminopropyl)-3'-O-cyclopentyldiosmetin

Treatment of the compound obtained in Example 1 with hydroxylamine yields the expected compound.
Melting point: 190°–193° C.

EXAMPLE 31

7-O-(2-Ethoxyiminocyclopentyl)-3'-O-cyclopentyldiosmetin

Treatment of the compound obtained in Example 9 with O-ethylhydroxylamine yields the expected compound.

EXAMPLE 32

7-O-[2-(N-Ethylimino)propyl]-3'-O-cyclopentyldiosmetin N-oxide

The compound obtained in Example 1 is treated with N-ethylhydroxylamine to yield the expected compound.

EXAMPLE 33

7-O-[2-(N-Ethylimino)cyclopentyl]-3'-O-cyclopentyldiosmetin N-oxide

Using the procedure described in the preceding example, starting from the compound of Example 9, the expected compound is obtained.

EXAMPLE 34

7-O-Ethoxycarbonylmethyl-3'-O-cyclpentyl-5-deoxydiosmetin

Carrying out the procedure described in Example 2, starting from 5-deoxydiosmetin obtained in Preparation B, the expected compound is obtained.
Melting point: 120°–121° C.

In the same way, carrying out the procedures of Examples 1 and 3 to 24 above and using 5-deoxydiosmetin in place of diosmetin, the compounds which follow are obtained.

EXAMPLE 35

7-O-(2-Oxopropyl)-3'-O-cyclopentyl-5-deoxydiosmetin

EXAMPLE 36

7-O-Cyanomethyl-3'-O-cyclopentyl-5-deoxydiosmetin

EXAMPLE 37

7-O-t-Butoxycarbonylmethyl-3'-O-cyclopentyl-5-deoxydiosmetin

EXAMPLE 38

7-O-(3-Ethoxycarbonylpropyl)-3'-O-cyclopentyl-5-deoxydiosmetin

EXAMPLE 39

7-O-Benzoylmethyl-3'-O-cyclopentyl-5-deoxydiosmetin

EXAMPLE 40

7-O-(4-Oxopentyl)-3'-O-cyclopentyl-5-deoxydiosmetin

EXAMPLE 41

7-O-(3-Oxo-2-butyl)-3'-O-cyclopentyl-5-deoxydiosmetin

EXAMPLE 42

7-O-(2-Oxocyclopentyl)-3'-O-cyclopentyl-5-deoxydiosmetin

EXAMPLE 43

7-O-(2-Oxobutyl)-3'-O-cyclopentyl-5-deoxydiosmetin

EXAMPLE 44

7-O-(Carboxymethyl)-3'-O-cyclopentyl-5-deoxydiosmetin

EXAMPLE 45

7-O-(N-Methoxy-N-methylaminocarbonylmethyl)-3'-O-cyclopentyl-5-deoxydiosmetin

EXAMPLE 46

7-O-Morpholinocarbonylmethyl-3'-O-cyclopentyl-5-deoxydiosmetin

EXAMPLE 47

7-O-(N,N-Diethylaminocarbonylmethyl)-3'-O-cyclopentyl-5-deoxydiosmetin

EXAMPLE 48

7-O-(N,N-Diethylaminothiocarbonylmethyl)-3'-O-cyclopentyl-5-deoxydiosmetin

EXAMPLE 49

7-O-[(4-Methyl-1-piperazinyl)carbonylmethyl]-3'-O-cyclopentyl-5-deoxydiosmetin

EXAMPLE 50

7-O-(N-Methylaminocarbonylmethyl)-3'-O-cyclopentyl-5-deoxydiosmetin

EXAMPLE 51

7-O-Aminocarbonylmethyl-3'-O-cyclopentyl-5-deoxydiosmetin

EXAMPLE 52

7-O-(N,N-Dimethylaminocarbonylmethyl)-3'-O-cyclopentyl-5-deoxydiosmetin

EXAMPLE 53

7-O-(N-Hydroxyaminocarbonylmethyl)-3'cyclopentyl-5-deoxydiosmetin

EXAMPLE 54

7-O-(Morpholinoethyl)-3'-O-cyclopentyl-5-deoxydiosmetin

EXAMPLE 55

7-O-[(4-Methyl-1-piperazinyl)ethyl]-3'-O-cyclopentyl-5-deoxydiosmetin

EXAMPLE 56

7-O-(N,N-Dimethylaminoethyl)-3'-O-cyclopentyl-5-deoxydiosmetin

EXAMPLE 57

7-O-(N,N,N Trimethylammonioethyl)-3'-O-cyclopentyl-5-deoxydiosmetin iodide

Carrying out the procedures described in the preceding examples, using 3'-O-(5-phenyl-2-pentyl)diosmetin obtained in Preparation C in place of 3'-O-cyclopentyldiosmetin, the compounds which follow are obtained.

EXAMPLE 58

7-O-(2-Oxopropyl)-3'-O-(5-phenyl-2-pentyl)diosmetin

EXAMPLE 59

7-O-Ethoxycarbonylmethyl-3'-O-(5-phenyl-2-pentyl)diosmetin

EXAMPLE 60

7-O-Cyanomethyl-3'-O-(5-phenyl-2-pentyl)diosmetin

EXAMPLE 61

7-O-t-Butoxycarbonylmethyl-3'-O-(5-phenyl-2-pentyl)diosmetin

EXAMPLE 62

7-O-(3-Ethoxycarbonylpropyl)-3'-O-(5-phenyl-2-pentyl)diosmetin

EXAMPLE 63

7-O-Benzoylmethyl-3'-O-(5-phenyl-2-pentyl)diosmetin

EXAMPLE 64

7-O-(4-Oxopentyl)-3'-O-(5-phenyl-2-pentyl)diosmetin

EXAMPLE 65

7-O-(3-Oxo-2-butyl)-3'-O-(5-phenyl-2-pentyl)diosmetin

EXAMPLE 66

7-O-(2-Oxocyclopentyl)-3'-O-(5-phenyl-2-pentyl)diosmetin

EXAMPLE 67

7-O-(2-Oxobutyl)-3'-O-(5-phenyl-2-pentyl)diosmetin

EXAMPLE 68

7-O-(Carboxymethyl)-3'-O-(5-phenyl-2-pentyl)diosmetin

EXAMPLE 69

7-O-(N-Methoxy-N-methylaminocarbonylmethyl)-3' (5-phenyl-2-pentyl) diosmetin

EXAMPLE 70

7-O-Morpholinocarbonylmethyl-3'-O-(5-phenyl-2-pentyl)diosmetin

EXAMPLE 71

7-O-(N,N-Diethylaminocarbonylmethyl)-3'-O-(5-phenyl-2-pentyl)diosmetin

EXAMPLE 72

7-O-(N,N-Diethylaminothiocarbonylmethyl)-3'-O-(5-phenyl-2-pentyl)diosmetin

EXAMPLE 73

7-O-[(4-Methyl-1-piperazinyl)carbonylmethyl]-3'-O-(5-phenyl-2-pentyl)diosmetin

EXAMPLE 74

7-O-(N-Methylaminocarbonylmethyl)-3'-O-(5-phenyl-2-pentyl)diosmetin

EXAMPLE 75

7-O-Aminocarbonylmethyl-3'-O-(5-phenyl-2-pentyl)diosmetin

EXAMPLE 76

7-O-(N,N-Diethylaminothiocarbonylmethyl)-3'-O-(5-phenyl-2-pentyl)diosmetin

EXAMPLE 77

7-O-(N-Hydroxyaminocarbonylmethyl)-3'-O-(5-phenyl-2-pentyl)diosmetin

EXAMPLE 78

7-O-(Morpholinoethyl)-3'-O-(5-phenyl-2-pentyl)diosmetin

EXAMPLE 79

7-O-[(4-Methyl-1-piperazinyl)ethyl]-3'-O-(5-phenyl-2-pentyl)diosmetin

EXAMPLE 80

7-O-(N,N-Dimethylaminoethyl)-3'-O-(5-phenyl-2-pentyl)diosmetin

EXAMPLE 81

7-O-(N,N,N-Trimethylammonioethyl)-3'-O-(5-phenyl-2-pentyl)diosmetin iodide

EXAMPLE 82

7-(N,N-Dimethylaminocarbonylmethyloxy)-5-hydroxy-4'-methoxy-3'-pentylflavone

Step a: 5,7-Dihydroxy-4'-methoxy-3'-pentylflavone

Using the procedure described in Preparation B, replacing 3-cyclopentyloxy-4-methoxybenzoyl chloride by 4-methoxy-3-pentylbenzoyl chloride, and 2,4-dihydroxyacetophenone by 2,4,6-trihydroxyacetophenone, the expected compound is obtained.

Melting point: 166°–168° C.

Step b: 7-(N,N-Dimethylaminocarbonylmethyloxy)-5-hydroxy-4'-methoxy-3'-pentylflavone Treatment of the compound obtained in the preceding step with N,N-dimethylchloroacetamide according to the procedure described in Example 1 yields the expected compound.

Meltng point: 112°–114° C.

The compounds which follow are obtained according to the procedures described above.

EXAMPLE 83

4'-Ethoxy-5-hydroxy-3'-(1-pentenyl)-7-(2-oxopropoxy)flavone

EXAMPLE 84

3'-O-Adamantyl-7-O-(2-oxopropyl)diosmetin

EXAMPLE 85

7-O-(N,N-Dimethylaminocarbonylmethyl)-3'-O-(exo-2-norbornyl)diosmetin

Melting point: 156°–157° C.

EXAMPLE 86

3'-Allyl-4'-methoxy-5-hydroxy-7-(2-oxopropoxy)flavone

EXAMPLE 87

3'-O-(2-Methylcyclopropylmethyl)-7-O-(2-oxopropyl)-5-deoxydiosmetin

EXAMPLE 88

3'-O-Cyclopentyl-7-O-(4-quinolylethyl)diosmetin

EXAMPLE 89

3'-O-Cyclopentyl-7-O-[(2-quinazolinyl)propyl]diosmetin

EXAMPLE 90

7-O-(N,N-Dimethylaminocarbonylmethyl)-3'-O-(3-methylbutyl)diosmetin

Melting point: 151°–153° C.

EXAMPLE 91

7-O-(N,N-Dimethylaminocarbonylmethyl)-3'-O-isopropyldiosmetin

Melting point: 190°–193° C.

EXAMPLE 92

3'-O-Allyl-7-O-(N,N-Dimethylaminocarbonylmethyl)diosmetin

Melting point: 202°–204° C.

EXAMPLE 93

7-O-(N,N-Dimethylaminocarbonylmethyl)-3'-O-pentyldiosmetin

Melting point: 181°–182° C.

EXAMPLE 94

7-O-(N-Benzyloxyaminocarbonylmethyl)-3'-O-cyclopentyldiosmetin

Melting point: 172°–174° C.

PHARMACOLOGICAL STUDY

EXAMPLE A: Measurement of PDE activity

U937 cells are cultured in a culture medium (RPMI) containing 10% of fetal calf serum. Briefly, the cells are lysed and then centrifuged (100,000 g, 60 min, 4° C.), and the supernatant is recovered for the purpose of separating the different forms of PDE by HPLC (C. Lugnier and V. B. Schini, *Biochem. Pharmacol.*, 39, (1990), 75–84).

The PDE activity is measured by the appearance of [$^3$H]5'-AMP resulting from hydrolysis of Cyclic [$^3$H]AMP. The PDE and Cyclic [$^3$H]AMP (1 µCi/ml) are incubated for 30 minutes at 30° C. The radioactivity is measured by means of a liquid scintillation counter (Beckman LS 1701).

PDE 4 is characterized by:
- the hydrolysis of cyclic AMP,
- the absence of inhibition by cyclic GMP of the hydrolysis of cyclic AMP, and
- inhibition by rolipram, a reference molecule.

The compounds are studied at two concentrations ($10^{-7}$M and $10^{-5}$M) in duplicate. The results are expressed as a % inhibition of phosphodiesterase activity. The compounds of the present invention display a very substantial inhibition of phosphodiesterase activity, which inhibition can, for example, exceed 60%, at a concentration as low as $10^{-7}$M.

EXAMPLE B: Pharmaceutical composition: tablets

Preparation formula for 1000 tablets containing a 1 mg dose of 7-O-(2-oxopropyl)-3'-O-cyclopentyldiosmetin.

| | |
|---|---|
| 7-O-(2-Oxypropyl)-3'-O-cyclopentyldiosmetin | 1 g |
| Wheat starch | 20 g |
| Cornstarch | 20 g |
| Lactose | 30 g |
| Magnesium stearate | 2 g |
| Silica | 1 g |
| Hydroxypropylcellulose | 2 g |

We claim:

1. A compound selected from those of general formula (I):

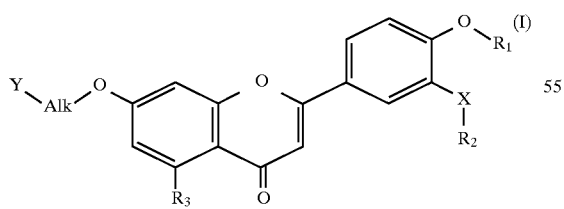

in which $R_1$ represents alkyl, $R_2$ is chosen from the group consisting of
  cyclic hydrocarbon containing 3 to 9 carbon atoms inclusive, optionally containing one or more intra-cyclic double bonds and optionally substituted with one or more halogen, alkyl, alkoxy and/or hydroxyl,
  polycyclic hydrocarbon containing 6 to 15 carbon atoms inclusive, optionally containing one or more double bonds and optionally substituted with one or more halogen, alkyl, alkoxy, and/or hydroxyl,
  linear or branched hydrocarbon containing 1 to 13 carbon atoms inclusive, optionally containing one or more unsaturations in the form of double and/or triple bonds and optionally substituted with one or more halogen, hydroxyl, alkoxy, aryl, heteroaryl radicals, cyclic hydrocarbon radicals defined as above and/or polycyclic hydrocarbon radicals defined above, $R_3$ is chosen from hydrogen and hydroxyl, Alk represents linear or branched alkylene containing 1 to 6 carbon atoms, inclusive X is chosen from oxygen, —CR,'= and —CHR'—, R' is chosen from hydrogen and alkyl, and Y is chosen from the group consisting of:

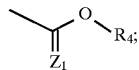

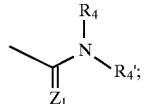

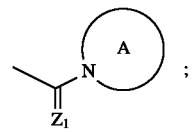

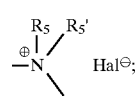

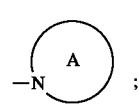

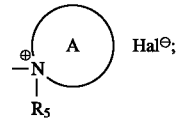

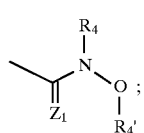

-continued

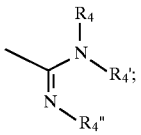

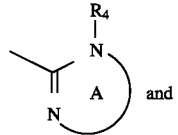 and

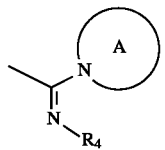

in which:

$Z_1$ represents oxygen or sulfur, $Z_2$ represents oxygen, sulfur, $=N-OR_4$, or

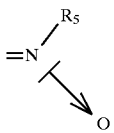

$R_4$, $R_4'$ and $R_4''$, which may be identical or different, are chosen, independently of one another, from hydrogen, alkyl optionally substituted with aryl or heteroaryl, aryl, heteroaryl, and cycloalkyl, $R_5$, $R_5'$ and $R_5''$, which may be identical or different, are chosen, independently of one another, from alkyl optionally substituted with aryl or heteroaryl, aryl, heteroaryl, and cycloalkyl, A represents a saturated or unsaturated mono- or bicyclic radical containing a total of 5 to 10 atoms (among which, in total, 1, 2, or 3 of them can optionally represent a hetero atom chosen from oxygen, sulfur, and/or nitrogen) and optionally substituted with one or more halogen, alkyl, and/or alkoxy, and Hal represents halogen, or alternatively the radicals -Alk-Y together form a radical chosen from the group consisting of:

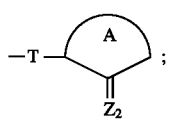

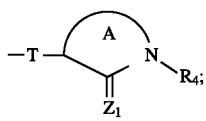

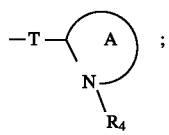

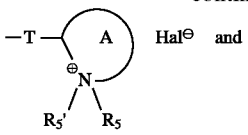

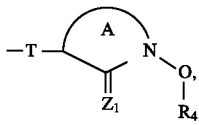

in which A, $R_4$, $R_5$, $R_5'$, $Z_1$, $Z_2$ and Hal are as defined above, and T represents either a bond or linear or branched alkylene containing 1 to 6 carbon atoms inclusive, on the understanding that, except where otherwise stated, the term "alkyl" represents alkyl containing 1 to 6 carbon atoms inclusive in an unbranched or branched chain, and optionally substituted with one or more halogen, hydroxyl, and/or alkoxy, the term "alkoxy" represents alkoxy containing 1 to 6 carbon atoms inclusive in an unbranched or branched chain, and optionally substituted with one or more halogen and/or hydroxyl, the term "aryl" represents phenyl or naphthyl, optionally substituted with one or more halogen, alkyl, hydroxyl, and/or alkoxy, the term "heteroaryl" represents a radical chosen from furyl, thienyl, thiazolyl, isothiazolyl, oxazolyl, isoxazolyl, pyrrolyl, imidazolyl, pyrazolyl, pyridyl, pyrazinyl, pyrimidyl, pyridazinyl, indolyl, quinolyl, isoquinolyl and quinazolinyl, optionally substituted with one or more halogen, alkyl, hydroxyl, and/or alkoxy, the term "halogen atom" represents fluorine, chlorine, bromine, or iodine, the term "cycloalkyl" represents a cyclic and saturated hydrocarbon containing 3 to 8 carbon atoms inclusive and optionally substituted with one or more halogen, and/or alkyl, hydroxyl, and/or alkoxy, its possible optical and/or geometric isomers in pure form or as a mixture, and its possible addition salts with a pharmaceutically-acceptable acid or base, with the proviso, however, that when $R_1$ represents methyl, X represents oxygen, $R_3$ represents hydrogen, Alk represents methylene, and Y represents $C(Z_1)OR_4$, wherein $Z_1$ represents oxygen and $R_4$ represents ethyl, then $R_2$ is other than unsubstituted alkyl.

2. A compound as claimed in claim 1 in which X represents oxygen, its possible optical and/or geometric isomers in pure form or as a mixture, as well as its possible addition salts with a pharmaceutically-acceptable acid or base.

3. A compound as claimed in claim 1 in which $R_2$ represents cyclopentyl, its possible optical and/or geometric isomers in pure form or as a mixture, as well as its possible addition salts with a pharmaceutically-acceptable acid or base.

4. The compound as claimed in claim 1 which is 7-O-(2-oxopropyl)-3'-O-cyclopentyl-diosmetin.

5. The compound as claimed in claim 1 which is 7-O-ethoxycarbonylmethyl-3'-O-cyclopentyldiosmetin.

6. The compound as claimed in claim 1 which is 7-O-(N,N-dimethylaminocarbonylmethyl)-3'-O-cyclopentyldiosmetin.

7. The compound as claimed in claim 1 which is 7-O-(N-methoxy-N-methylamino-carbonylmethyl)-3'-O-cyclopentyldiosmetin.

8. The compound as claimed in claim 1 which is 7-O-(N-methylaminocarbonylmethyl)-3'-O-cyclopentyldiosmetin.

9. The compound as claimed in claim 1 which is 7-O-(N,N-dimethylaminocarbonylmethyl)-3'-O-(exo-2-norbornyl)diosmetin.

10. A method for treating a living body afflicted with a condition requiring a Group IV phosphodiesterase inhibitor comprising the step of administering to the living body an amount of a compound of claim 1 which is effective for alleviation of said conditions.

11. A pharmaceutical composition useful as a Group IV phosphodiesterase inhibitor method comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,889,003
DATED : March 30, 1999
INVENTOR(S) : A. Dhainaut, G. Lewin, E. Canet, M. Lonchampt, Y. Rolland Page 1 of 3

It is certified that error appears in the above-indentified patent and that said Letters Patent is hereby corrected as shown below:

Column 9, line 46 (approx.): "-Cyclopentyidiosmetin" should read -- -Cyclopentyldiosmetin --.

Column 10, line 9: "-cyclopentyidiosmetin" should read -- -cyclopentyldiosmetin --.

Column 11, line 47 (approx.): "-cyclopentyidiosmetin" should read -- -cyclopentyldiosmetin --.

Column 12, line 4: "cyclopentyidiosmetin" should read -- cyclopentyldiosmetin --.

Column 12, line 6: "-cyclopentyidiosmetin" should read -- -cyclopentyldiosmetin.

Column 12, line 21: "-cyclopentyidiosmetin" should read -- -cyclopentyldiosmetin.

Column 15, line 46: "-cyclpentyl-5-" should read -- -cyclopentyl-5- --.

Column 17, line 27: At the beginning of the line, "3'" should read -- 3'-O- --.

Column 18, line 54: At the end of the line, "-3'" should read -- -3'-O- --.

UNITED STATES PATENT AND TRADEMARK OFFICE
CERTIFICATE OF CORRECTION

PATENT NO. : 5,889,003
DATED : March 30, 1999
INVENTOR(S) : A. Dhainaut, G. Lewin, E. Canet, M. Lonchampt, Y. Rolland Page 2 of 3

It is certified that error appears in the above-indentified patent and that said Letters Patent is hereby corrected as shown below:

Column 21, line 67: Insert a -- , -- (comma) after the word "alkoxy".

Column 22, line 12: Insert a -- , -- (comma) after the word "above" at the beginning of the line.

Column 22, line 13: Insert the word -- as -- between "defined" and "above".

Column 23, line 11(approx.): Insert a -- , -- (comma) between the formula and the word "and".

Column 24, line 1(approx.): Insert a -- , -- (comma) between "Hal$^\ominus$" and the word "and".

Column 24, line 46 thru 50: Beginning with "$R_1$" and ending with "alkyl." delete these lines, and insert the following:  -- $R_2$ is an unsubstituted or hydroxy-substituted linear or branched hydrocarbon, then Y is other than $C(Z_1)OR_4$. --

UNITED STATES PATENT AND TRADEMARK OFFICE
CERTIFICATE OF CORRECTION

PATENT NO. :     5,889,003
DATED      :     March 30, 1999
INVENTOR(S) :    A. Dhainaut, G. Lewin, E. Canet, M. Lonchampt, Y. Rolland It is certified that error appears in the above-indentified patent and that said Letters Patent is hereby corrected as shown below:

Column 26, line 3:  At the end of the line, "conditions." should read -- condition. --.

Column 26, line 5:  Delete the word "method".

Signed and Sealed this

Second Day of November, 1999

Attest:

Q. TODD DICKINSON

*Attesting Officer*          *Acting Commissioner of Patents and Trademarks*